US012559570B2

(12) United States Patent
Saito et al.

(10) Patent No.: US 12,559,570 B2
(45) Date of Patent: Feb. 24, 2026

(54) ANTI-PAD2 ANTIBODY

(71) Applicant: PHARMA FOODS INTERNATIONAL CO., LTD., Kyoto (JP)

(72) Inventors: Kenji Saito, Kyoto (JP); Tomoko Sakata, Kyoto (JP); Takaaki Kawanobe, Kyoto (JP); Keita Koga, Kyoto (JP)

(73) Assignee: PHARMA FOODS INTERNATIONAL CO., LTD., Kyoto (JP)

( * ) Notice: Subject to any disclaimer, the term of this patent is extended or adjusted under 35 U.S.C. 154(b) by 698 days.

(21) Appl. No.: 16/972,832

(22) PCT Filed: Jun. 19, 2019

(86) PCT No.: PCT/JP2019/024310
§ 371 (c)(1),
(2) Date: Dec. 7, 2020

(87) PCT Pub. No.: WO2019/244934
PCT Pub. Date: Dec. 26, 2019

(65) Prior Publication Data
US 2021/0246225 A1      Aug. 12, 2021

(30) Foreign Application Priority Data
Jun. 20, 2018      (JP) ................................. 2018-117142

(51) Int. Cl.
*C07K 16/40*          (2006.01)
*C12N 9/78*          (2006.01)
(52) U.S. Cl.
CPC ................ *C07K 16/40* (2013.01); *C12N 9/78* (2013.01); *C12Y 305/03006* (2013.01); *C07K 2317/34* (2013.01); *C07K 2317/92* (2013.01)
(58) Field of Classification Search
CPC ............ C07K 16/40; C12Y 305/03006; C12Y 305/03015
See application file for complete search history.

(56) References Cited

U.S. PATENT DOCUMENTS

| | | | | |
|---|---|---|---|---|
| 2004/0110938 A1* | 6/2004 | Parekh | ................... | A61P 25/00 |
| | | | | 514/21.4 |
| 2010/0151486 A1 | 6/2010 | Guo et al. | | |
| 2010/0239588 A1 | 9/2010 | Guo et al. | | |
| 2011/0003880 A1* | 1/2011 | Sanjoy | | |
| 2011/0243945 A1* | 10/2011 | Raats | ................... | A61P 25/00 |
| | | | | 514/21.4 |
| 2014/0127720 A1 | 5/2014 | Rosen et al. | | |
| 2015/0376294 A1 | 12/2015 | Nielsen et al. | | |
| 2023/0203193 A1 | 6/2023 | Weber | | |

FOREIGN PATENT DOCUMENTS

| | | | | |
|---|---|---|---|---|
| CN | 104360070 A | 2/2015 | | |
| WO | WO-2005100604 A2 * | 10/2005 | ........... | C12Q 1/6883 |
| WO | WO-2009033743 A1 * | 3/2009 | ............. | C07K 16/18 |
| WO | WO-2014086365 A1 * | 6/2014 | ............. | C07K 16/40 |
| WO | WO-2016/155745 A1 | 10/2016 | | |

OTHER PUBLICATIONS

Novus Biologicals: PADI2 Antibody catalogue No. NBP1-54958 (retrieved from: PADI2 Antibody (NBP1-54958): Novus Biologicals) (as cited on IDS) (Year: 2023).*
Damgaard et al., "Generation of monoclonal antibodies against peptidylarginine deiminase 2 (PAD2) and development of a PAD2-specific enzyme-linked immunosorbent assay," J. Immunol. Methods 405:15-22 (2014) (cited on the IDS) (Year: 2014).*
PADI2 Gene-Peptidyl Arginine Deiminase 2, GeneCards, retrieved from: https://www.genecards.org/cgi-bin/carddisp.pl?gene=PADI2 (Year: 2023).*
Peptide Modifications, GeneScript, retrieved from: https://www.genscript.com/peptide_modification.html#:~:text=Peptide%20antigens%20are%20often%20too%20small%20to%20generate,albumin%20%28BSA%29%2C%20ovalbumin%2C%20or%20keyhole%20limpet%20hemocyanin%20%28KLH%29 (Year: 2008).*
Wayback Machine Proof of date of availability for Peptide Modifications, GeneScript retrieved from wayback machine.com (Year: 2023).*
Leenaars, M. and Hendriksen, C. F. M., Critical Steps in the Production of Polyclonal and Monoclonal Antibodies: Evaluation and Recommendations, ILAR Journal, https://doi.org/10.1093/ilar.46.3.269 (Year: 2005).*
Q9Y2J8-PADI2_Human, Uniprot, retrieved from: https://www.uniprot.org/uniprotkb/Q9Y2J8/entry (accessed Sep. 8, 2023) (Year: 2023).*
Wimmers, F., et al., Monitoring of Dynamic Changes in Keyhole Limpet Hemocyanin (KLOH)-specific B cells in KLH-vaccinated Cancer Patients, Sci Rep 7, 43486 (2017). https://doi.org/10.1038/srep43486 (Year: 2017).*
Janeway et al (Immunobiology: The Immune System in Health and Disease. 5th edition. New York: Garland Science; 2001. The generation of diversity in immunoglobulins. Available from: https://www.ncbi.nlm.nih.gov/books/NBK27140/) (Year: 2001).*
Goel et al. (2004, J. Immunol. 173: 7358-7367) (Year: 2004).*
Khan et al. (2014, J. Immunol. 192: 5398-5405) (Year: 2014).*
Poosarla et al. (2017, Biotechn. Bioeng. 114(6): 1331-1342) (Year: 2017).*
Bawadekar et al., "Peptidylarginine deiminase 2 is required for tumor necrosis factor alpha-induced citrullination and arthritis, but not neutrophil extracellular trap formation," J. Autoimmunity 80:39-47 (2017).

(Continued)

*Primary Examiner* — Gregory S Emch
*Assistant Examiner* — Ashley H. Gao
(74) *Attorney, Agent, or Firm* — Clark & Elbing LLP

(57)          ABSTRACT

To obtain an anti-PAD2 antibody having excellent PAD2 inhibitory activity. Provided is an anti-PAD2 antibody that specifically binds to positions 341 to 357 of PAD2. Also provided is an anti-PAD2 antibody that specifically binds to a peptide consisting of an amino acid sequence set forth in SEQ ID NO: 1.

25 Claims, 2 Drawing Sheets

Specification includes a Sequence Listing.

(56) References Cited

OTHER PUBLICATIONS

International Search Report and Written Opinion mailed Aug. 6, 2019 for PCT International Application No. PCT/JP2019/024310, Saito et al., "Novel Anti-PAD2 Antibody," filed Jun. 19, 2019 (7 pages).

Moscarello et al., "The role of citrullinated proteins suggests a novel mechanism in the pathogenesis of multiple sclerosis," Neurochem. Res. 32(2):251-256 (2007).

Sohn et al., "Local joint inflammation and histone citrullination in a murine model of the transition from preclinical autoimmunity to inflammatory arthritis," Arthritis Rheumatol. 67(11):2877-2887 (2015).

Antibodies-Online, "anti-PADI2 antibody (Peptidyl Arginine Deiminase, Type II) (Middle Region)," <https://www.antibodies-online.com/antibody/631162/anti-Peptidyl+Arginine+Deiminase,+Type+II+PADI2+Middle+Region+antibody/>, last updated Jan. 11, 2022, noted on EESR as published on Oct. 20, 2011 (4 pages).

Aosasa et al., "Epitope-based chicken-derived novel anti-PAD2 monoclonal antibodies inhibit citrullination," J. Immunol. Res. 2021:6659960 (2021) (10 pages).

Damgaard et al., "Generation of monoclonal antibodies against peptidylarginine deiminase 2 (PAD2) and development of a PAD2-specific enzyme-linked immunosorbent assay," J. Immunol. Methods 405:15-22 (2014).

Extended European Search Report dated Feb. 1, 2022, for European Patent Application No. 19823371.0, Saito et al., "Novel Anti-PAD2 Antibody," filed Jun. 19, 2019 (8 pages).

Novus Biologicals, "PADI2 Antibody," <https://www.novusbio.com/products/padi2-antibody_nbp1-54958#datasheet>, retrieved on Jan. 11, 2022, noted on EESR as published on Jan. 1, 2008 (3 pages).

"PADI2 Polyclonal antibody," Proteintech. <https://ptgen.com/products/PADI2,PAD2-Antibody-12110-1-AP.htm>, includes datasheet (Jul. 2012) (13 pages).

"protein-arginine deiminase type-2 [Homo sapiens]," GenBank. NCBI Reference Sequence: NP_031391.2 (Jun. 2018) (3 pages).

Antibodies-Online, "anti-PADI2 antibody (Peptidyl Arginine Deiminase, Type II) (Middle Region)," <https://www.antibodies-online.com/antibody/631162/anti-Peptidyl+Arginine+Deiminase,+Type+II+PADI2+Middle+Region+antibody/>, Oct. 20, 2011 (3 pages).

Cherrington et al., "Potential role for PAD2 in gene regulation in breast cancer cells," PLoS One. 7(7):e41242 (Jul. 2012) (12 pages).

Dong, Antibody Engineering. Beijing Medical University Publishing House. vol. 1. 16-17 (Jun. 2002) (4 pages).

Li et al., "Relationship between PADI2 and genetic susceptibility in various human tumors," Journal of Shandong University (Health Sciences). 55(11):47-53 (English abstract) (Nov. 2017).

Novus Biologicals, "PADI2 Antibody," <https://www.novusbio.com/products/padi2-antibody_nbp1-54958#datasheet>, with Safety Data Sheet, Jan. 1, 2008 (8 pages).

Office Action dated Apr. 27, 2023, for Chinese Patent Application No. 201980038636.6, Saito et al., "Novel Anti-PAD2 Antibody," filed Jun. 19, 2019 (English translation) (26 pages).

Yang, Animal Immunology. China Agricultural University Press Publisher. vol. 2. 14-15 (Aug. 2003) (4 pages).

"Peptide Polyclonal Antibodies as an Alternative to Monoclonal Antibodies (mabs)," Everest Biotech Ltd. Retrieved from <https://web.archive.org/web/20160912092114/https:/everestbiotech.com/peptide-polyclonal-antibodies-alternative-monoclonal-antibodies-mabs/> (2016) (1 page).

"Protein vs Peptide Antigens," Pacific Immunology. Retrieved from <https://www.pacificimmunology.com/resources/antigens/protein-vs-peptide-antigens/> (2014) (2 pages).

Ayter et al., "Peptide Antibodies: New Tools for Cell Biology and Medicine," Mikrobiyol Bült. 22:76-85 (1988) (English abstract) (5 pages).

Shinnick et al., "Synthetic peptide immunogens as vaccines," Annu Rev Microbiol. 37:425-46 (1983).

Trier et al., "Peptide Antibodies in Clinical Laboratory Diagnostics," Adv Clin Chem. 81:43-96 (Feb. 2017).

"De Novo Antibody Sequencing Process: An Overview," Abterra Biosciences. <https://abterrabio.com/2018/08/06/de-novo-antibody-sequencing-an-overview/>, Aug. 6, 2018 (3 pages).

"Polyclonal vs. Monoclonal Antibodies," Proteintech. <https://www.ptglab.com/news/blog/polyclonal-vs-monoclonal-antibodies/>, Dec. 13, 2017, accessed on Jun. 14, 2020 (3 pages).

* cited by examiner

Fig. 3

◆ PAD2 epitope analysis   [▨] → EC50 twice or larger than toward the original sequence    ※ND : Not determined

| SEQ ID NO: | 341 | 342 | 343 | 344 | 345 | 346 | 347 | 348 | 349 | 350 | 351 | 352 | 353 | 354 | 355 | 356 | 357 | Original sequence |
|---|---|---|---|---|---|---|---|---|---|---|---|---|---|---|---|---|---|---|
| Amino acid | Y | L | N | R | G | D | R | W | I | Q | D | E | I | E | F | G | Y | |
| anti-PAD2 mAb S4 | 6.12 | | | 42.72 | | | 1.66 × 10⁴ | | | N.D. | | | 105.90 | | | 9.17 | | 4.46 |
| anti-PAD2 mAb S10 | 6.18 | | | 35.82 | | | 659.80 | | | 6.25 × 10² | | | 1.84 × 10³ | | | 9.08 | | 4.49 |
| anti-PAD2 mAb S24 | 7.15 | | | 123.90 | | | 1550.00 | | | 119.70 | | | 280.70 | | | 9.16 | | 5.08 |
| anti-PAD2 mAb S103 | 4.93 | | | 12.96 | | | 50.09 | | | N.D. | | | 1.30 × 10³ | | | 5.76 | | 4.16 |
| anti-PAD2 mAb S178 | 3.01 | | | 553.30 | | | 1.24 × 10⁴ | | | 6.42 × 10² | | | N.D. | | | 4.35 | | 2.15 |
| anti-PAD2 mAb S209 | 19.25 | | | 296.80 | | | 332.80 | | | N.D. | | | N.D. | | | 31.90 | | 11.53 |

ANTI-PAD2 ANTIBODY

SEQUENCE LISTING

The instant application contains a Sequence Listing which has been submitted electronically in ASCII format and is hereby incorporated by reference in its entirety. Said ASCII copy, created Dec. 7, 2020, is named 51007-020001_Sequence_Listing_12.07.20_ST26 and is 7,735 bytes in size.

TECHNICAL FIELD

The present invention relates to novel anti-PAD2 antibodies.

BACKGROUND ART

Peptidylarginine deiminase 2 (PAD2) has been known as an enzyme involving citrullination of an arginine residue(s) in proteins. This citrullination is a reaction in which arginine, the most basic amino acid among amino acids of proteins, is converted to neutral citrulline, and is thus important for the structures and reactions of such proteins.

Some reports have been made on the association between the citrullination by PAD2 and diseases. For instance, Non-Patent Literature 1 discloses (in Abstract) that PAD2 participates in TNFα-induced citrullination and arthritis. Non-Patent Literature 2 discloses (in Abstract) that myelin basic protein citrullination involves a biochemical pathway for the onset of multiple sclerosis. Non-Patent Literature 3 discloses (in Abstract) the relationship between histone citrullination and the onset of arthritis.

Patent Literature 1 describes that a mouse was immunized with rabbit PAD2 to prepare an anti-PAD2 antibody(s) (Example 1); the antibody(s) bound to positions 1 to 165 of human PAD2 (Example 3); and the PAD2 inhibitory activity of the antibody(s) was tested (Example 4).

CITATION LIST

Patent Literature

[Patent Literature 1] WO 2014/086365

Non Patent Literature

[Non-Patent Literature 1] "Peptidylarginine deiminase 2 is required for tumor necrosis factor alpha-induced citrullination and arthritis, but not neutrophil extracellular trap formation.", Bawadekar et al., J Autoimmun. 2017 June; 80:39-47.
[Non-Patent Literature 2] "The role of citrullinated proteins suggests a novel mechanism in the pathogenesis of multiple sclerosis.", Moscarello et al., Neurochem Res. 2007 February; 32 (2): 251-6. Epub 2006 Sep. 22.
[Non-Patent Literature 3] "Local Joint inflammation and histone citrullination in a murine model of the transition from preclinical autoimmunity to inflammatory arthritis." Sohn et al., Arthritis Rheumatol. 2015 November; 67 (11): 2877-87.

SUMMARY OF INVENTION

Technical Problem

Unfortunately, the anti-PAD2 antibodies in the above Patent Literature 1 fail to have sufficiently strong PAD2 inhibitory activity. Thus, there has been a room for improvement. Besides, no antibody having excellent PAD2 inhibitory activity has been reported.

The present invention has been made in light of the above situations. The purpose of the invention is to provide an anti-PAD2 antibody having excellent PAD2 inhibitory activity, etc.

Solution to Problem

The present inventors have prepared an anti-PAD2 antibody(s) by using, as an antigen, a peptide (positions 341 to 357 of PAD2) consisting of an amino acid sequence set forth in SEQ ID NO: 1 as described in Examples below. Next, how the resulting antibodies reacted with PAD2 were checked. Then, surprisingly, the antibodies exhibited excellent inhibitory activity toward PAD2. In particular, each antibody exerts markedly better unexpected PAD2 inhibitory activity than anti-PAD2 antibodies (#2 and #34) prepared based on the above Patent Literature 1. Specifically, an aspect of the present invention provides an anti-PAD2 antibody that specifically binds to positions 341 to 357 of peptidylarginine deiminase 2 (PAD2). Use of this antibody enables detection of PAD2. Use of this antibody makes it possible to inhibit a function of PAD2.

Another aspect of the invention provides an anti-PAD2 antibody that specifically binds to a peptide consisting of an amino acid sequence set forth in SEQ ID NO: 1. Use of this antibody enables detection of PAD2. Use of this antibody makes it possible to inhibit a function of PAD2.

Another aspect of the present invention provides an anti-PAD2 antibody that specifically binds to positions 344 to 357 of PAD2. Use of this antibody enables detection of PAD2. Use of this antibody makes it possible to inhibit a function of PAD2.

Another aspect of the invention provides a polynucleotide or vector that encodes the above anti-PAD2 antibody. Another aspect of the invention provides a composition comprising the above anti-PAD2 antibody. Another aspect of the invention provides an inhibitor for citrullination activity of PAD2, comprising the above anti-PAD2 antibody. Another aspect of the invention provides a method for producing an anti-PAD2 antibody, comprising the step of growing a cell comprising the above polynucleotide or vector.

According to embodiments of the invention, the KD (M) toward the above PAD2 may be $9.0 \times 10^{-8}$ or less; a site of the binding may be a binding site identified by alanine scanning in which three amino acids are replaced; the above anti-PAD2 antibody may be a monoclonal antibody; or the above anti-PAD2 antibody may be an antigen-binding fragment.

BRIEF DESCRIPTION OF DRAWINGS

FIG. 3 is a diagram showing the results of assessing epitopes of anti-PAD2 antibodies used in Examples.

DESCRIPTION OF EMBODIMENTS

Figure 1:
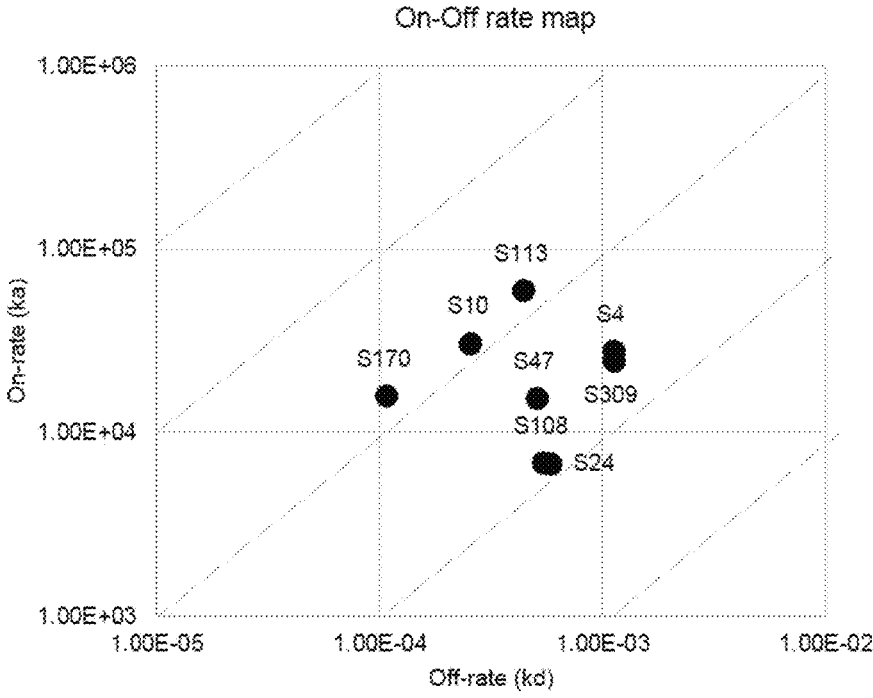
FIG. 1 is a plot showing the results of measuring affinities of anti-PAD2 antibodies used in Examples.

Hereinafter, embodiments of the invention will be described in detail. Note that repeated descriptions of the same content are omitted, if appropriate, so as to avoid redundancy.

An embodiment of the invention provides a novel anti-PAD2 antibody. This antibody is, for instance, an anti-PAD2 antibody that specifically binds to positions 341 to 357 of PAD2. Alternatively, the above antibody may be an anti-PAD2 antibody that specifically binds to a peptide consisting of an amino acid sequence set forth in SEQ ID NO: 1. Otherwise, the anti-PAD2 antibody may specifically bind to positions 344 to 357 of PAD2. Use of this antibody makes it possible to, for instance, inhibit a function of PAD2.

PAD2 has been generally known as an enzyme involving citrullination of an arginine residue(s) in proteins. The details of the amino acid sequence of PAD2, etc., can be seen in the Web sites of NCBI (National Center for Biotechnology Information), HGNC (HUGO Gene Nomenclature Committee), or others. For instance, the accession number of PAD2 as described in NCBI is NP 031391.2. The amino acid sequence of PAD2 is, for instance, SEQ ID NO: 2. If PAD2 has PAD2 activity, the biological origin is not limited. Examples of PAD2 include PAD2 derived from a human, monkey, mouse, rat, dog, or cat. Positions 341 to 357 of PAD2 typically have, in sequence, Y, L, N, R, G, D, R, W, I, Q, D, E, I, E, F, G, and Y (one-letter amino acid code).

The "anti-PAD2 antibody" in an embodiment of the invention includes an antibody that can bind to PAD2. A method for producing this anti-PAD2 antibody is not particularly limited, and the antibody may be produced by immunizing a mammal or bird with PAD2. An anti-PAD2 antibody that specifically binds to positions 341 to 357 of PAD2 may be produced by immunizing a mammal or bird with, for instance, a peptide consisting of the amino acid sequence set forth in SEQ ID NO: 1. An anti-PAD2 antibody that specifically binds to positions 344 to 357 or 344 to 355 of PAD2 may be produced by immunizing a mammal or bird with, for instance, a peptide consisting of the amino acid sequence set forth in SEQ ID NO: 1 or a peptide consisting of the amino acid sequence at positions 4 to 17 or 4 to 15 of SEQ ID NO: 1. The anti-PAD2 antibody that specifically binds to positions 344 to 357 or 344 to 355 of PAD2 may be obtained by optionally comprising a step of selecting an anti-PAD2 antibody that can bind to a wild-type PAD2, but cannot bind to a PAD2 mutant having some of positions 344 to 357 or 344 to 355 each replaced by Ala.

An anti-PAD2 antibody according to an embodiment of the invention may be an antibody that inhibits a function of PAD2. The functional inhibition involves a citrullination activity inhibition. An anti-PAD2 antibody according to an embodiment of the invention may be an antibody that binds to a calcium-binding form of PAD2 or an antibody that inhibits a function of the calcium-binding form of PAD2. An anti-PAD2 antibody according to an embodiment of the invention may have a PAD2 activity inhibitory function. An anti-PAD2 antibody according to an embodiment of the invention may be an antibody that binds to a calcium-bound PAD2 or may have a calcium-bound PAD2 activity inhibitory function.

An anti-PAD2 antibody according to an embodiment of the invention may be a monoclonal antibody. The monoclonal antibody could act on PAD2 more efficiently than a polyclonal antibody. From the viewpoint of efficiently producing an anti-PAD2 monoclonal antibody with a desired effect, a chicken is preferably immunized with PAD2.

Unless otherwise indicated, examples of PAD2 used as an antigen include the full-length PAD2 or a peptide fragment of PAD2.

The antibody class of an anti-PAD2 antibody according to an embodiment of the invention is not particularly limited and may be, for instance, IgM, IgD, IgG, IgA, IgE, or IgY. In addition, the subclass of the antibody is not particularly limited and may be, for instance, IgG1, IgG2, IgG3, IgG4, IgA1, or IgA2.

An anti-PAD2 antibody according to an embodiment of the invention may be an antibody fragment having PAD2-binding activity (hereinafter, sometimes referred to as an "antigen-binding fragment"). This case can elicit an effect of increasing stability or production efficiency of antibody and so on.

An anti-PAD2 antibody according to an embodiment of the invention may be a fusion protein. This fusion protein may have a polypeptide or oligopeptide bound to the N or C terminal of PAD2. Here, the oligopeptide may be a His tag. Also, the fusion protein may be obtained by fusing a part(s) of mouse, human, or chicken antibody sequence. Such a fusion protein may be included in a form of anti-PAD2 antibody according to this embodiment.

An anti-PAD2 antibody according to an embodiment of the invention may be an antibody produced by undergoing a step of immunizing a chicken with PAD2.

An anti-PAD2 antibody according to an embodiment of the invention may have a KD (M) between any two values of, for instance, $9.0 \times 10^{-8}$, $7.0 \times 10^{-8}$, $5.0 \times 10^{-8}$, $3.0 \times 10^{-8}$, $1.0 \times 10^{-8}$, $9.0 \times 10^{-9}$, $7.0 \times 10^{-9}$, $5.0 \times 10^{-9}$, $3.0 \times 10^{-9}$ or less.

An anti-PAD2 antibody according to an embodiment of the invention may be an antibody that binds to a wild-type PAD2 or a PAD2 mutant. Examples of the mutant include those having an SNP(s), etc., that caused by variation in individual DNA sequences. The amino acid sequence of the wild-type or mutant PAD2 may have preferably 80% or higher, more preferably 90% or higher, still more preferably 95% or higher, or particularly preferably 98% or higher homology to the amino acid sequence set forth in SEQ ID NO: 2.

The "anti-PAD2 antibody that specifically binds to positions 341 to 357 of PAD2" according to an embodiment of the invention involves an antibody that binds to a region within the amino acids at positions 341 to 357 of PAD2. As long as this antibody can bind to, for instance, a peptide consisting of the amino acid sequence set forth in SEQ ID NO: 1, the site within positions 341 to 357 of PAD2 recognized by the antibody is not limited. Examples of this antibody include an antibody that specifically binds to, for instance, an epitope including at least one amino acid at positions 341 to 357 of PAD2. Examples of this antibody include an antibody that specifically binds to positions 344 to 357 of PAD2. The "anti-PAD2 antibody that specifically binds to positions 344 to 357 of PAD2" according to an embodiment of the invention involves an antibody that binds to a region within the amino acids at positions 344 to 357 of PAD2. Examples of this antibody include an antibody that specifically binds to an epitope including at least one amino acid at positions 344 to 357 of PAD2. Examples of this antibody include an antibody that specifically binds to positions 344 to 346, 347 to 349, 350 to 352, 353 to 355, or 356 to 357 of PAD2. In addition, examples of this antibody include an antibody that specifically binds to positions 344 to 355 of PAD2. The "anti-PAD2 antibody that specifically binds to positions 344 to 355 of PAD2" according to an embodiment of the invention involves an antibody that binds to a region within the amino acids at positions 344 to 355 of PAD2. Examples of this antibody include an antibody that specifically binds to an epitope including at least one amino acid at positions 344 to 355 of PAD2. Examples of this antibody include an antibody that specifically binds to positions 344 to 346, 347 to 349, 350 to 352, or 353 to 355 of PAD2. In addition, examples of this antibody include an antibody that specifically binds to positions 347 to 355 of PAD2. The "anti-PAD2 antibody that specifically binds to positions 347 to 355 of PAD2" according to an embodiment of the invention involves an antibody that binds to a region within the amino acids at positions 347 to 355 of PAD2. Examples of this antibody include an antibody that specifically binds to an epitope including at least one amino acid at positions 347 to 355 of PAD2. Examples of this antibody include an antibody that specifically binds to positions 347 to 349, 350 to 352, or 353 to 355 of PAD2.

An anti-PAD2 antibody according to an embodiment of the invention may be an antibody that can bind to a wild-type PAD2, but cannot bind to a PAD2 mutant having some of positions 344 to 357 each replaced by Ala. The "PAD2 mutant having some of positions 344 to 357 each replaced by Ala" according to an embodiment of the invention involves an antibody against a mutant form of PAD2 having any of positions 344 to 346, 347 to 349, 350 to 352, 353 to 355, 356 to 357, or 344 to 355 each replaced by Ala. In this regard, however, in the mutant form of PAD2 having some of positions 344 to 357 each replaced by Ala, positions other than positions 344 to 346, 347 to 349, 350 to 352, 353 to 355, or 356 to 357 are herein not necessarily replaced. The wording "cannot bind to" in an embodiment of the invention refers to the wording "cannot substantially bind to". In addition, this includes the case of the wording "cannot significantly bind to". Further, the case where $EC_{50}$ toward an analyte is twice or larger than $EC_{50}$ toward the wild-type counterpart may be evaluated as "cannot bind to". At this time, the case where $EC_{50}$ is "Not Determined" may be evaluated as "cannot bind to". Furthermore, the case where binding to an analyte is 50% or less than binding to the wild-type counterpart may be evaluated as "cannot bind to".

An anti-PAD2 antibody according to an embodiment of the invention may be an antibody, $EC_{50}$ of which toward a mutant form of PAD2 having some of positions 344 to 357 each replaced by Ala is twice or larger than $EC_{50}$ toward the wild-type PAD2. An anti-PAD2 antibody according to an embodiment of the invention may be an antibody, $EC_{50}$ of which toward a mutant form of PAD2 having some of positions 344 to 357 each replaced by Ala is twice or larger than $EC_{50}$ in the case of using an anti-PAD2 polyclonal antibody. As used herein, the wording "twice or larger" may mean, for instance, 2, 3, 4, 5, 10, 100, 105, 1010, or 1015, or a number between any two thereof. The case where $EC_{50}$ is "Not Determined" may be evaluated as "twice or larger". The reactivity may be assessed by, for instance, ELISA or surface plasmon resonance. The "anti-PAD2 polyclonal antibody" according to an embodiment of the invention includes, for instance, serum. The binding or reactivity involves affinity.

An anti-PAD2 antibody according to an embodiment of the invention may be an antibody, the binding of which to a mutant form of PAD2 having some of positions 344 to 357 each replaced by Ala is 50% or less than binding to the wild-type PAD2. An anti-PAD2 antibody according to an embodiment of the invention may be an antibody, the binding of which to a mutant form of PAD2 having some of positions 344 to 357 each replaced by Ala is 50% or less than binding in the case of using an anti-PAD2 polyclonal antibody. As used herein, the wording "50% or less" may mean, for instance, 50, 45, 40, 35, 30, 25, 20, 15, 10, 5, 1, or 0% or a number between any two thereof. An anti-PAD2 antibody according to an embodiment of the invention may be an antibody produced by a production process including the steps of: selecting an antibody that can significantly bind to a wild-type PAD2; and selecting an antibody that cannot bind to a mutant form of PAD2 having some of positions 344 to 357 each replaced by Ala.

An anti-PAD2 antibody according to an embodiment of the invention can bind to other amino acid residue(s) within an epitope as long as the antibody can specifically bind to positions 341 to 357 of PAD2. The antibody that specifically binds to a specific site may be an antibody that recognizes the specific site.

An anti-PAD2 antibody according to an embodiment of the invention may be an antibody that specifically binds to an epitope within positions 341 to 357 of PAD2. An anti-PAD2 antibody according to an embodiment of the invention may be an antibody that specifically binds to an epitope including positions 341 to 357 of PAD2. An anti-PAD2 antibody according to an embodiment of the invention can bind to an amino acid residue(s) other than an epitope within positions 341 to 357 of PAD2.

An anti-PAD2 antibody according to an embodiment of the invention may be an antibody that can bind to a peptide having the amino acid sequence set forth in SEQ ID NO: 1, but cannot bind to at least one peptide having any of the amino acid sequences set forth in SEQ ID NOs: 3 to 8. An anti-PAD2 antibody according to an embodiment of the invention may be an antibody that cannot bind to a form of PAD2, the positions 341 to 357 of which are deleted.

An anti-PAD2 antibody according to an embodiment of the invention may be an antibody, $EC_{50}$ of which toward at least one peptide having any of amino acid sequences set forth in SEQ ID NOs: 3 to 8 is twice or larger than $EC_{50}$ toward the wild-type PAD2. An anti-PAD2 antibody according to an embodiment of the invention may be an antibody, $EC_{50}$ of which toward at least one peptide having any of amino acid sequences set forth in SEQ ID NOs: 3 to 8 is twice or larger than $EC_{50}$ in the case of using an anti-PAD2 polyclonal antibody.

An anti-PAD2 antibody according to an embodiment of the invention may be an antibody, the binding of which to at least one peptide having any of amino acid sequences set forth in SEQ ID NOs: 3 to 8 is 50% or less of binding to the wild-type PAD2. An anti-PAD2 antibody according to an embodiment of the invention may be an antibody, the binding of which to at least one peptide having any of amino acid sequences set forth in SEQ ID NOs: 3 to 8 is 50% or less than binding in the case of using an anti-PAD2 polyclonal antibody.

An anti-PAD2 antibody according to an embodiment of the invention may be an antibody that specifically binds to positions 4 to 17 or 4 to 15 of a peptide having the amino acid sequence set forth in SEQ ID NO: 1. This antibody may be able to bind to other amino acid residue(s) within an epitope as long as the antibody can bind to positions 4 to 17 or 4 to 15 of a peptide having the amino acid sequence set forth in SEQ ID NO: 1. Note that the "antibody that specifically binds to a peptide" in an embodiment of the invention involves an antibody that can specifically bind to a peptide. The antibody that specifically binds to a peptide may be able to bind to another compound while the antibody has one binding property identified and can bind to the peptide. The "antibody that specifically binds to a peptide having the amino acid sequence set forth in SEQ ID NO: 1" involves an antibody that can bind to the full-length PAD2 while the antibody can specifically bind to the peptide. This likewise applies to an antibody that specifically binds to positions 4 to 17 or 4 to 15 of a peptide having the amino acid sequence set forth in SEQ ID NO: 1.

The site of binding of the anti-PAD2 antibody in an embodiment of the invention may be assessed by, for instance, alanine scanning. As used herein, the "alanine scanning" is a technique for characterizing an antibody that binds to a protein while an amino acid(s) of the protein, for instance, is each replaced by alanine. The assessment by alanine scanning may include, for instance (i) a step of replacing three amino acid residues of an antigen each by Ala to produce an Ala mutant; (ii) a step of measuring affinity of a test antibody toward the Ala mutant; and/or (iii) a step of determining, as a binding site, an amino acid residue(s) before the Ala replacement in the Ala mutant without significant reactivity toward the test antibody. This assessment enables identification of the binding site. The above step (i) may include a step of preparing a plurality of Ala mutants while a plurality of three amino acid residues of the antigen are independently replaced by Ala. This assessment method optionally includes a step (iv) of measuring affinity of the test antibody toward a wild-type PAD2 or measuring affinity of an anti-PAD2 polyclonal antibody toward the Ala mutant. This assessment method also optionally include a step (v) of: determining that the test antibody does not exhibit significant reactivity when a value for $EC_{50}$ of the test antibody at the time of measuring affinity of the test antibody toward the Ala mutant is twice or larger than a value for $EC_{50}$ of the test antibody at the time of measuring affinity of the test antibody toward the wild-type counterpart; or determining that the test antibody does not exhibit significant reactivity when a value for $EC_{50}$ of the test antibody at the time of measuring affinity of the test antibody toward the Ala mutant is twice or larger than a value for $EC_{50}$ of the test antibody at the time of measuring affinity of the test antibody toward the Ala mutant by using an anti-PAD2 polyclonal antibody. The alanine scanning may be performed by three-amino-acid substitution. At this time, when the number of amino acids included in the antigen is indivisible by three, this end of the antigen may be replaced by two amino acids. The antigen used for alanine scanning may be PAD2 or a peptide fragment thereof. The affinity may be assessed by, for instance, ELISA or surface plasmon resonance.

An anti-PAD2 antibody according to an embodiment of the invention may be an antibody that specifically binds to an epitope including positions 347 to 354 of PAD2. An anti-PAD2 antibody according to an embodiment of the invention may be an antibody that specifically binds to an epitope including position 351, 352, 353, or 354 of PAD2. This antibody may be able to bind to other amino acid residue(s) within the epitope as long as the antibody can bind to position 351, 352, 353, or 354 of PAD2. An anti-PAD2 antibody according to an embodiment of the invention may be an antibody that specifically binds to position 8, 9, 10, or 11 of a peptide having the amino acid sequence set forth in SEQ ID NO: 1. This antibody may be able to bind to other amino acid residue(s) within the epitope as long as the antibody can bind to position 8, 9, 10, or 11 of the peptide. An anti-PAD2 antibody according to an embodiment of the invention may be an antibody that cannot specifically bind to a mutant from of PAD2 having an Ala mutation at position 351, 352, 353, or 354 of PAD2. From the viewpoint of citrullination inhibition potential, it is preferable that the antibody recognizes, in particular, position 351, 352, 353, or 354 of PAD2. At that time, the binding may be assessed by alanine scanning such that one amino acid residue is replaced by Ala.

As used herein, the term "antibody" includes a molecule or population thereof that can specifically bind to a specific epitope on an antigen. In addition, the antibody may be a polyclonal or monoclonal antibody. The antibody may be present in various forms, and examples include at least one form selected from the group consisting of full-length antibodies (antibodies with Fab and Fc regions), Fv antibodies, Fab antibodies, F(ab')$_2$ antibodies, Fab' antibodies, diabodies, single-chain antibodies (e.g., scFv), dsFv, multivalent antibodies (e.g., bivalent antibodies), antigen binding peptides or polypeptides, chimeric antibodies, mouse antibodies, chicken antibodies, humanized antibodies, human antibodies, or their equivalents (or equivalents). In addition, the antibody may include a modified antibody or an intact antibody. The modified antibody may be an antibody bound to each molecule such as polyethylene glycol. The modified antibody may be obtained by chemically modifying an antibody using a known procedure. The amino acid sequence, class, or subclass of the antibody may be derived from, for instance, a human, a non-human mammal (e.g., a rat, mouse, rabbit, cow, monkey), or a bird (e.g., a chicken). In addition, examples of the antibody include an isolated antibody, a purified antibody, or a recombinant antibody. Further, the antibody may be used, for instance, in vitro or in vivo.

As used herein, the "polyclonal antibody" may be generated by administering an immunogen containing an antigen of interest to, for instance, a mammal (e.g., a rat, mouse, rabbit, cow, monkey) or a bird (e.g., a chicken). The immunogen may be administered by injecting at least one immunizing agent or adjuvant. The adjuvant may be used to augment immune response and may contain Freund's adjuvant (complete or incomplete), mineral gel (e.g., aluminum hydroxide), or a surfactant (e.g., lysolecithin). The immunization protocol has been known in the art and may be implemented by any procedure in which immune response is induced in accordance with a host organism chosen (Protein Experiment Handbook, YODOSHA CO., LTD., (2003): 86-91).

As used herein, the term "monoclonal antibody" includes an antibody in the case where individual antibodies constituting a population substantially react with the identical epitope. Also, the monoclonal antibody may be an antibody in the case where individual antibodies constituting a population are substantially the same (provided that naturally occurring mutations are permitted). The monoclonal antibody is highly specific and differs from a regular polyclonal antibody typically including different antibodies against distinct epitopes. The method for preparing a monoclonal antibody is not particularly limited, and the monoclonal antibody may be prepared by substantially the same method as the hybridoma method described in, for instance, "Kohler G, Milstein C., Nature. 1975 Aug. 7; 256(5517): 495-497". Alternatively, the monoclonal antibody may be prepared by substantially the same method as the recombinant method disclosed in U.S. Pat. No. 4,816,567. In addition, the monoclonal antibody may be isolated from a phage antibody library by using substantially the same method as the technology described in "Clackson et al., Nature. 1991 Aug. 15; 352(6336): 624-628" or "Marks et al., J Mol Biol. 1991 Dec. 5; 222(3): 581-597". Further, the method described in "Protein Experiment Handbook, YODOSHA CO., LTD. (2003): 92-96" may be used for the preparation.

As used herein, the term "Fv antibody" refers to an antibody including an antigen-recognition site. This region comprises one heavy-chain variable domain and one light-chain variable domain that are noncovalently bonded. In this structure, three CDRs of each variable domain interact with each other to be able to form an antigen-binding site on a surface of the VH-VL dimer.

As used herein, the term "Fab antibody" refers to an antibody obtained by, for instance, treating an antibody containing Fab and Fc regions with a protease papain to give fragments, in which about a half of the H chain on the N-terminal side and the whole L chain are bonded via a disulfide bond. The Fab can be obtained by, for instance, digesting, with a protease papain, an anti-PAD2 antibody containing Fab and Fc regions in the above embodiment of the invention.

As used herein, the term "F(ab')$_2$ antibody" refers to an antibody obtained by, for instance, treating an antibody containing Fab and Fc regions with a protease pepsin to give fragments, in which two Fab comparable portions are included. The F(ab')$_2$ can be obtained by, for instance, digesting, with a protease pepsin, an anti-PAD2 antibody containing Fab and Fc regions in the above embodiment of the invention. Alternatively, the Fab' portions below may be bonded via a thioether bond or disulfide bond for the production.

As used herein, the term "Fab' antibody" refers to an antibody obtained by, for instance, cleaving a disulfide bond in the hinge region of F(ab')$_2$. The Fab' antibody may be obtained by, for instance, treating F(ab')$_2$ with a reductant dithiothreitol.

As used herein, the term "scFv antibody" refers to an antibody in which VH and VL are linked via a suitable peptide linker. The scFv antibody may be produced by, for instance, obtaining cDNA encoding a VH and a VL of an anti-PAD2 antibody according to the above embodiment of the invention, constructing a polynucleotide encoding the VH-peptide linker-VL, cloning the polynucleotide into a vector, and using cells for its expression.

As used herein, the term "diabody" refers to an antibody having divalent antigen-binding activities. The divalent antigen-binding activities may be the same, or one of the antigen-binding activities may be different from the other. The diabody can be produced by, for instance, constructing a polynucleotide encoding an scFv such that the length of amino acid sequence of its peptide linker is 8 residues or less, cloning the resulting polynucleotide into a vector, and using cells for its expression.

As used herein, the term "dsFv" refers to an antibody obtained by constructing a polypeptide while a cysteine residue is introduced into each of a VH or a VL and bonding, via a disulfide bond, the above cysteine residues. Where each cysteine residue is introduced may be selected based on an antibody conformation prediction in accordance with the method indicated by Reiter and colleagues (Reiter et al., Protein Eng. 1994 May; 7 (5): 697-704).

As used herein, the term "antigen-binding peptide or polypeptide" refers to an antibody structured by including a VH and/or a VL of an antibody, or CDRs 1, 2, and/or 3 thereof. The peptide containing multiple CDRs may be bonded directly or via a suitable peptide linker(s).

The method for producing the above Fv antibody, Fab antibody, F(ab')$_2$ antibody, Fab' antibody, scFv antibody, diabody, dsFv antibody, or antigen-binding peptide or polypeptide (hereinafter, sometimes referred to as "Fv antibody, etc.") is not particularly limited. For instance, DNA encoding a region of Fv antibody, etc., in an anti-PAD2 antibody according to the above embodiment of the invention may be cloned into an expression vector and cells for its expression may be used for the production. Alternatively, a chemical synthesis process such as Fmoc method (fluorenylmethyl-oxycarbonyl method) or tBOC method (t-butyloxycarbonyl method) may be used for the production. Note that an antigen-binding fragment in the above embodiment of the invention may be at least one kind of the above Fv antibody, etc.

As used herein, the term "chimeric antibody" may be obtained by, for instance, linking variable regions of an antibody and a constant region of a xenogeneic antibody and can be prepared by gene recombinant technology. Examples include a mouse/human chimeric antibody, a chicken/human chimera antibody, or a chicken/mouse chimera antibody. The mouse/human chimeric antibody can be produced by, for instance, the method described in "Roguska et al., Proc Natl Acad Sci USA. 1994 Feb. 1; 91(3): 969-973". In a basic method for producing the mouse/human chimeric antibody, a mouse leader sequence and variable region sequences present in a cloned cDNA are linked to a sequence encoding a human antibody constant region already present in a mammalian expression vector. Alternatively, a mouse leader sequence and variable region sequences present in a cloned cDNA may be linked to a sequence encoding a human antibody constant region, and this may be integrated into a mammalian expression vector. A fragment of human antibody constant region may be a H-chain constant region or a L-chain constant region of any human antibody. Examples of the human H-chain constant region include Cγ1, Cγ2, Cγ3, or Cγ4. Examples of the L-chain constant region include Cλ or Cκ.

As used herein, the term "humanized antibody" refers to an antibody that has, for instance, at least one non-human CDR and human immunoglobulin-derived framework region, and a human immunoglobulin-derived constant region and can bind to a desired antigen. For antibody humanization, it is possible to use various techniques known in the art. As used herein, the term "human antibody" refers to an antibody in which variable and constant regions of a heavy chain and variable and constant regions of a light chain of an antibody, for instance, are derived from a gene encoding a human immunoglobulin. To produce a human antibody, it is possible to use various techniques known in the art.

An anti-PAD2 antibody according to an embodiment of the invention may have a form of scFv. In this case, a linker may be provided between a heavy chain and a light chain. Examples of the representative linker include, but are not limited to, a sequence containing 0 to 5 amino acids composed of G and/or P. The linker is dispensable and is not necessarily present.

As used herein, the "amino acid" is a general term for any organic compound having an amino group and a carboxyl group. When an antibody according to an embodiment of the invention contains a "specific amino acid sequence", any of amino acids in the amino acid sequence may be chemically modified. In addition, any of amino acids in the amino acid sequence may form a salt or a solvate. In addition, any of amino acids in the amino acid sequence may be in an L-form or D-form. In such cases, an antibody according to an embodiment of the invention can be said to contain the above "specific amino acid sequence". Examples of the known in vivo chemical modification of amino acids contained in a protein include N-terminal modification (e.g., acetylation, myristoylation), C-terminal modification (e.g., amidation, glycosylphosphatidylinositol addition), or side-chain modification (e.g., phosphorylation, glycosylation).

An embodiment of the invention provides a polynucleotide or vector encoding an anti-PAD2 antibody according to the above embodiment of the invention. This polynucleotide or vector may be introduced into a cell to produce a transformant. The transformant may be a human cell or a non-human mammalian (e.g., rat, mouse guinea pig, rabbit, cow, monkey) cell. Examples of the mammalian cell include Chinese hamster ovary cells (CHO cells), monkey cell COS-7, or human embryonic kidney cells (e.g., HEK293 cells). Alternatively, the transformant may be *Escherichia coli*, yeast, or the like. The above polynucleotide or vector may be constructed to be able to express an anti-PAD2 antibody. The above polynucleotide or vector may contain, for instance, elements necessary for protein expression, such as a promoter, an enhancer, a replication origin, and/or an antibiotic resistance gene. The above polynucleotide or vector may have an exogenous nucleotide sequence. Examples of the exogenous nucleotide sequence include nucleotide sequences derived from two or more species selected from the group consisting of human and non-human organisms (e.g., bacteria, archaea, yeast, insects, birds, viruses, or mammals other than humans).

Examples of the above vector that can be used include *E. coli* plasmids (e.g., pET-Blue), *Bacillus subtilis* plasmids (e.g., pUB110), yeast plasmids (e.g., pSH19), expression plasmids for animal cells (e.g., pA1-11, pcDNA3.1-V5/His-TOPO), bacteriophages such as λ phage, or viral vectors. The vector may be an expression vector or linear.

Examples of an available method for introducing the above polynucleotide or vector into a cell include a calcium phosphate method, lipofection, electroporation, an adenoviral method, a retroviral method, or microinjection (the revised fourth ed., New Gene Engineering Handbook, YODOSHA CO., LTD., (2003): 152-179). Examples of an available method for producing an antibody by using a cell include methods described in "Protein Experiment Handbook, YODOSHA CO., LTD., (2003); 128-142)".

An embodiment of the invention provides a method for producing an anti-PAD2 antibody, comprising the step of growing a cell comprising the polynucleotide or vector according to the above embodiment of the invention. The above growing step includes a culturing step. In addition, this production process may include a step of collecting the anti-PAD2 antibody. Further, this production process may include a step of preparing a cell culture medium. Furthermore, this production process may include a step of purifying the anti-PAD2 antibody.

For purification of an antibody in an embodiment of the invention, it is possible to use, for instance, ammonium sulfate or ethanol precipitation, Protein A, Protein G, or gel filtration chromatography, anion or cation exchange chromatography, phosphocellulose chromatography, hydrophobic interaction chromatography, affinity chromatography, hydroxylapatite chromatography, or lectin chromatography (Protein Experiment Handbook, YODOSHA CO., LTD., (2003): 27-52).

An embodiment of the invention provides a composition comprising the anti-PAD2 antibody according to the above embodiment of the invention. Use of this composition allows for efficient detection of PAD2. In addition, it is possible to efficiently inhibit citrullination by PAD2. Components included in this composition are not particularly limited and may include, for instance, a buffer. At least one of the below-described embodiments (e.g., optionally including a carrier) regarding inhibitors and/or pharmaceutical compositions is applicable to this composition.

An embodiment of the invention provides an inhibitor for citrullination activity of PAD2, comprising the anti-PAD2 antibody according to the above embodiment of the invention. Use of this inhibitor makes it possible to efficiently inhibit citrullination by PAD2. A rate of decrease in the citrullination activity by the above inhibitor may be 20, 30, 40, 60, 80% or higher, or may be a number between any two thereof. This rate of decrease may be represented in a relative percentage while the decrease rate when PBS is used is set to 0%. An "agent" in an embodiment of the invention may include, for instance, a composition used for research and treatment. Examples of the above inhibitor include a therapeutic agent. The above inhibitor may be used, for instance, in vitro or in vivo. The above inhibitor may contain the composition according to the above embodiment of the invention. An embodiment of the invention provides a method for inhibiting citrullination activity of PAD2, comprising the step of causing PAD2 to contact the anti-PAD2 antibody according to the above embodiment of the invention. An embodiment of the invention provides a method for inhibiting citrullination activity of PAD2, comprising the step of administering, to a patient, the anti-PAD2 antibody according to the above embodiment of the invention. The above inhibition method involves an inhibition protocol implemented for research or treatment. An embodiment of the invention provides use of the anti-PAD2 antibody according to the above embodiment of the invention in the manufacture of an inhibitor for citrullination activity of PAD2. Examples of a citrullinated protein in an embodiment of the invention include, but are not particularly limited to, a protein with an arginine residue(s). Examples of this protein include a histone or myelin basic protein.

An embodiment of the invention provides a pharmaceutical composition comprising the anti-PAD2 antibody according to the above embodiment of the invention. This pharmaceutical composition optionally contains at least one pharmaceutically acceptable carrier. Examples of the pharmaceutical composition include a pharmaceutical composition for treatment of arthritis, rheumatoid arthritis, or multiple sclerosis. The above pharmaceutical composition may contain the composition according to the above embodiment of the invention. An embodiment of the invention provides a method for treating a disease, comprising the step of administering, to a patient, the anti-PAD2 antibody (or a pharmaceutical composition comprising the anti-PAD2 antibody) according to the above embodiment of the invention. Examples of the treatment include treatment of arthritis, rheumatoid arthritis, multiple sclerosis, or Sjogren's syndrome. Because of strong inhibition of histone citrullination, the anti-PAD2 antibody such as S4 described in Examples below is particularly effective in treatment of arthritis or rheumatoid arthritis. In addition, the anti-PAD2 antibody such as S4 can strongly inhibit citrullination of myelin basic protein, and is thus particularly effective in treatment of multiple sclerosis. An embodiment of the invention provides use of the anti-PAD2 antibody according to the above embodiment of the invention in the manufacture of a pharmaceutical composition.

An embodiment of the invention provides a PAD2 detection reagent comprising the anti-PAD2 antibody according to the above embodiment of the invention. Use of this reagent allows for efficient detection of PAD. An embodiment of the invention provides a PAD2 detection method comprising the step of causing a test sample to contact the anti-PAD2 antibody according to the above embodiment of the invention. An embodiment of the invention provides a kit comprising the anti-PAD2 antibody according to the above embodiment of the invention. Use of this kit allows for treatment or diagnosis of disease or detection of PAD2. This kit may contain, for instance, the composition, inhibitor, pharmaceutical composition, diagnostic agent, or detection reagent according to the above embodiment of the invention and optionally includes a package insert, a buffer, a container, or a package.

The "treatment" in an embodiment of the invention involves optionally exerting an effect of ameliorating, suppressing, or preventing a disease or at least one symptom accompanied by the disease. The "therapeutic agent" in an embodiment of the invention may be a pharmaceutical composition comprising an active ingredient and at least one pharmaceutically acceptable carrier. The "pharmaceutical composition" in an embodiment of the invention may be produce by any procedure known in the art of formulation, which procedure includes mixing, for instance, an active ingredient and the above carrier(s). In addition, a dosage form of the pharmaceutical composition is not limited as long as it can be used for treatment, and may be an active ingredient alone or may be a mixture of an active ingredient and any component(s). Also, the form of the above carrier is not particularly limited, and may be, for instance, a solid or liquid (e.g., a buffer). The content of the above carrier may be, for instance, a pharmaceutically effective amount. The effective amount may be, for instance, an amount sufficient to pharmaceutically stabilize or deliver the active ingredient. For instance, the buffer is effective in stabilization of the active ingredient in a vial. The dose, dosing interval, and/or administration method are not particularly limited, and may be selected, if appropriate, in view of the age, body weight, symptom, and/or affected organ of a patient. It is also preferable to contain a therapeutically effective amount or effective amount of the active ingredient so as to elicit a desired action.

An embodiment of the invention provides a method for promoting a function of a composition to inhibit citrullination activity, comprising the step of increasing, in the composition, a ratio of an anti-PAD2 antibody that specifically binds to positions 341 to 357 of PAD2. An embodiment of the invention provides a composition comprising an anti-PAD2 antibody, wherein 90% or higher of anti-PAD2 antibody molecules in the composition are an anti-PAD2 antibody that specifically binds to positions 341 to 357 of PAD2. An embodiment of the invention provides an antibody population comprising an anti-PAD2 antibody, wherein 90% or higher of anti-PAD2 antibody molecules in the antibody population are an anti-PAD2 antibody that specifically binds to positions 341 to 357 of PAD2. The wording "90% or higher" may mean, for instance, 90, 95, 96, 97, 98, 99% or higher, or 100% or a number between any two thereof.

An embodiment of the invention provides a peptide consisting of an amino acid sequence set forth in SEQ ID NO: 1. Use of this peptide makes it possible to produce an antibody that can bind to PAD2. Also, it is possible to detect an antibody that can bind to PAD2. The peptide consisting of an amino acid sequence set forth in SEQ ID NO: 1 may be chemically modified (e.g. KLH modification). Such a chemically modified peptide is included in a form of peptide comprising an amino acid sequence set forth in SEQ ID NO: 1. The peptide consisting of an amino acid sequence set forth in SEQ ID NO: 1 may be an isolated, purified, or concentrated peptide.

An embodiment of the invention provides an antigen composition comprising a peptide consisting of an amino acid sequence set forth in SEQ ID NO: 1. This antigen composition optionally contains, for instance, a buffer or adjuvant. An embodiment of the invention provides a method for producing an anti-PAD2 antibody, comprising the step of immunizing a mammal or bird with a peptide consisting of an amino acid sequence set forth in SEQ ID NO: 1. An embodiment of the invention provides a method for producing an anti-PAD2 antibody, comprising the step of causing an antibody or antibody library to contact a peptide consisting of an amino acid sequence set forth in SEQ ID NO: 1. An embodiment of the invention provides a method for detecting a PAD2-binding antibody, comprising the step of causing an anti-PAD2-antibody-containing test sample to contact a peptide consisting of an amino acid sequence set forth in SEQ ID NO: 1. An embodiment of the invention provides a composition for detection of an antibody that binds to active PAD2, comprising a peptide consisting of an amino acid sequence set forth in SEQ ID NO: 1.

As used herein, the "binding" may be mediated by either a covalent bond or noncovalent bond, and may involve, for instance, an ion bond, a hydrogen bond, a hydrophobic interaction, or a hydrophilic interaction.

As used herein, the term "significant(ly)" may mean a state of $p<0.05$ or $p<0.01$ when a statistically significant difference is applied in a Student's t-test for evaluation. Alternatively, the term may refer to a state where a substantial difference occurs.

All the literatures and (patent or patent application) publications cited are herein incorporated by reference in its entirety.

As used herein, the term "or" is used when "at least one" matter listed in the text is acceptable. The same applies to "or". When the wording "number between any two" is indicated herein, this range encompasses the two numbers inclusive. The wording "from A to B" herein means A or more and B or less.

Hereinabove, embodiments of the invention have been described. However, they are examples of the invention. Hence, it is possible to employ various configurations other than the above. In addition, the configurations described in the above embodiments may be combined and adopted.

EXAMPLES

Hereinbelow, the invention will be described in more detail with reference to Examples. However, the invention is not limited to them.

<Example 1> To Produce Anti-PAD2 Antibody

Three 3-month-old Boris Brown chickens were each intraperitoneally immunized with 333 μg of a KLH-conjugated peptide antigen (SEQ ID NO: 1; positions 341 to 357 of PAD2). Complete Freund's adjuvant (014-09541, Wako) for primary immunization and incomplete Freund's adjuvant (011-09551, Wako) for secondary or tertiary immunization were used with the antigen for immunization. For quaternary immunization, the antigen diluted with PBS (phosphate buffered saline) was intravenously injected. Blood was collected from the wing vein every other week, and the antibody titer was checked by ELISA. After the tertiary immunization, the quaternary immunization was conducted as the final immunization. Three days after the final immunization, the spleen of each chicken was removed; lymphocytes were isolated by density gradient centrifugation using Ficoll- Paque PLUS (17-1440-03, GE Healthcare); and a TRIzole reagent (15596026, Life Technologies) was used to extract RNA. The extracted RNA was subjected to RT-PCR using a PrimeScript II 1st Strand cDNA Synthesis Kit (6210A, TAKARA) to synthesize cDNA. Then, an scFv phage library was prepared. As its expression vector, an expression vector pPDS, in which a chicken 2 chain was inserted instead of a mouse K chain, was used. The scFv phage library was prepared in accordance with the method described in a reference document: "Nakamura et al., J Vet Med Sci. 2004 Ju; 66 (7): 807-814".

The scFv phage antibody library was used to perform panning using a plate on which the full-length PAD2 had been immobilized. The panning was performed in accordance with the method described in a reference document: "Nakamura et al., J Vet Med Sci. 2004 Ju; 66 (7): 807-814". After the fifth panning, the reactivity of the library was checked by ELISA using a plate on which a synthetic peptide was immobilized. A phage screening was conducted using the library with increased reactivity. During the screening, *E. coli* cells were infected with their phages, and experiments. These antibodies were hereinafter sometimes collectively referred to as "S4, etc.".

<Example 2> To Evaluate Reactivity of Anti-PAD2 Antibody (2-1) ELISA

ELISA was carried out under the following conditions to evaluate the reactivity of S4, etc., toward human PAD2.

(2-1-1) Materials

Antibodies: anti-PAD2 antibodies (S4, S10, S24, S47, S108, S113, S170, and S309), anti-PAD2 antibodies disclosed in WO/2014/086365 (#2 and #34), an anti-dinitrophenyl (DNP) antibody (a negative control antibody). The above #2 and #34 antibodies were created, based on the amino acid sequences of the variable regions disclosed in Examples of WO/2014/086365, and were then used (the same applies to the following Examples).

Antigen: the full-length human PAD2 antigen.

(2-1-2) Experimental Conditions

TABLE 1

| 1 Antigen immobilized: | 50 μL/well | O/N, @ 4° C. | 1 μg/mL full-length human PAD2 |
|---|---|---|---|
| 2 Blocking: | 250 μL/well | 60 min, @ 37° C. | 25% Block Ace/PBS |
| 3 Primary antibody: | 50 μL/well | 60 min, @ 37° C. | 200 ng/mL of each antibody diluted 4-fold with 10% Block Ace/PBS |
| 4 Secondary antibody: | 50 μL/well | 60 min, @ 37° C. | HRP-anti-mouse IgG (H + L) in 10% Block Ace/PBS (1:1000) |
| 5 Chromogenic substrate: | 50 μL/well | 30 min, @ RT | TMB (manufactured by KPL, Inc.) |
| 6 To stop coloring: | 50 μL/well | | TMB-stop solution (manufactured by KPL, Inc.) |
| 7 Measurement: | Wavelength at 450 nm/650 nm | | | plated on a 2×YT Agar plate(s) containing ampicillin (50 μg/ml, NACALAI TESQUE, INC.). Each of the resulting colonies was cultured in 2×YT liquid medium containing ampicillin. After infection with a helper phage, phage induction was carried out in 2×YT liquid medium containing ampicillin (50 μg/ml), kanamycin (25 μg/ml, Meiji Seika, Inc.), and IPTG (100 μg/ml, NACALAI TESQUE, INC.). The reactivity of the resulting scFv phage antibody in the culture supernatant was checked by ELISA using an antigen-immobilized plate. Each positive clone obtained was sequenced using a DNA sequencer (ABI PRISM 3100-Genetic Analyzer, Applied Biosystems) to determine the sequence.

Clones with different sequences were each subjected to PCR while the DNA strand encoding each scFv antibody was used as a template to amplify the H-chain variable region and the L-chain variable region of the chicken-derived antibody gene. Next, the resulting PCR product was digested with NheI restriction enzyme (R0157S, R0131S, BioLabs). Then, each H-chain variable region or each H-chain variable region was cloned into a mouse/chicken chimera antibody (igG1) expression vector likewise digested (H-chain expression vector: pcDNA4/myc-His; L-chain expression vector: pcDNA3/myc-His, Invitrogen). The H-chain and L-chain constructs produced were transfected into a CHO cell. After that, the reactivity was checked by ELISA using the full-length PAD2 immobilized. The vector disclosed in Tateishi et al., J Vet Med Sci. 2008 April; 70(4): 397-400 was used as the mouse chimera expression vector. Of the resulting antibody clones, S4, S10, S24, S47, S108, S113, S170, and S309 were used in the following (2-1-3) Results From the results of ELISA for each anti-PAD2 antibody, the value for 50% effective concentration ($EC_{50}$) was determined. Table 2 shows the results. A smaller value indicates higher reactivity. Any of the antibodies exhibited high reactivity toward PAD2.

TABLE 2

| | $EC_{50}$ (ng/mL) |
|---|---|
| S4 | 7.9 |
| S10 | 2.7 |
| S24 | 10.7 |
| S47 | 3.5 |
| S108 | 4.8 |
| S113 | 3.0 |
| S170 | 16.1 |
| S309 | 30.8 |
| #2 | 26.2 |
| #34 | 1.9 |

(2-2) Biacore

Biacore (GE Healthcare, Biacore T200) was used to evaluate the affinity of S4, etc., toward human PAD2.

(2-2-1) Materials

Antibodies: anti-PAD2 antibodies (S4, S10, S24, S47, S108, S113, S170, and S309)

Antigen: the full-length human PAD2 antigen.

(2-2-2) Protocol

Biacore (GE Healthcare, Biacore T200) was used to evaluate the affinity of S4, etc., toward human PAD2. The affinity was measured using a Mouse Antibody Capture Kit (GE Healthcare, BR-1008-38). Specifically, in accordance with the standard protocol provided by the manufacturer, NHS/EDC was used and amine coupling utilizing a free carboxyl group on a CM5 chip surface was conducted to immobilize a rabbit anti-mouse polyclonal antibody on the CM5 chip surface. Next, S4, etc., was captured on the rabbit anti-mouse polyclonal antibody. Then, human PAD2 at a varied concentration was applied on Biacore T200 to plot a kinetic sensorgram.

(2-2-3) Results

Table 3 and FIG. 1 show the results of measuring the affinity. Any of the antibodies exhibited high affinity toward PAD2.

TABLE 3

| Affinity (by Biacore assay) toward human PAD2 | | | |
| --- | --- | --- | --- |
| | ka (1/Ms) | kd (1/s) | KD (M) |
| S4 | $2.90 \times 10^4$ | $1.00 \times 10^{-3}$ | $2.63 \times 10^{-8}$ |
| S10 | $3.19 \times 10^4$ | $2.49 \times 10^{-4}$ | $7.80 \times 10^{-9}$ |
| S24 | $7.01 \times 10^3$ | $5.65 \times 10^{-4}$ | $8.07 \times 10^{-8}$ |
| S47 | $1.60 \times 10^4$ | $4.91 \times 10^{-4}$ | $3.07 \times 10^{-8}$ |
| S108 | $7.18 \times 10^3$ | $5.29 \times 10^{-4}$ | $7.36 \times 10^{-8}$ |
| S113 | $6.18 \times 10^4$ | $4.30 \times 10^{-4}$ | $6.96 \times 10^{-9}$ |
| S170 | $1.64 \times 10^4$ | $1.04 \times 10^{-4}$ | $6.33 \times 10^{-9}$ |
| S309 | $2.54 \times 10^4$ | $1.08 \times 10^{-3}$ | $4.27 \times 10^{-8}$ |

<Example 3> To Evaluate Potential of Anti-PAD2 Antibody to Inhibit Citrullination The following conditions were used to measure the potential of each anti-PAD2 antibody to inhibit citrullination activity of PAD2.

(3-1) Materials

Recombinant protein: crude fraction containing the full-length recombinant human PAD2.

Substrate: BAEE (Na-benzoyl-L-arginine ethyl ester hydrochloride).

Antibodies: an anti-dinitrophenyl (DNP) antibody (a negative control), anti-PAD2 antibodies (S4, S10, S24, S47, S108, S113, S170, and S309), an anti-PAD2 antibody disclosed in WO/2014/086365 (#34).

(3-2) Protocol

First, 5 μL of antibody solution was prepared using each anti-PAD2 antibody (S4, S10, S24, S47, S108, S113, S170, S309), #34 antibody, or anti-DNP antibody (negative control) at 1 to 6000 nM. Next, 5 μL of 3.75 ng/μL (50 nM) human PAD2 was prepared. Then, these solution, Tris-HCl buffer (pH 7.6), NaCl, and DTT were mixed in the total volume of 44 μL. The resulting solution was allowed to stand for 30 min. After that, 5 μL of 100 mM BAEE (benzoyl-arginine ethyl ester) and 1 μL of 0.05 M CaCl$_2$) were added and mixed well at the same time. This solution had a total volume of 50 μL and contained, as the final concentration, 20 mM Tris-HCl (pH 7.6), 150 mM NaCl, 1 mM DTT, 10 mM BAEE, 1 mM CaCl$_2$), 5 nM human PAD2, and each antibody at 0.1-600 nM. The solution was allowed to stand at 37° C. for 4 h. Then, 12.5 μL of 5 M perchloric acid was added to stop the reaction. The resulting citrullinated BAEE contained in this solution was subjected to colorimetry.

(3-3) Results

Table 4 shows the antibody concentration (EC$_{50}$) that imparted 50% activity inhibition to human PAD2. The case where the antibody concentration was below 600 nM and it was impossible to calculate the antibody concentration that imparted 50% activity inhibition was denoted as ND (Not Determined). The antibodies such as S4, etc., were demonstrated to have a higher potential to inhibit the activity than #34 antibody.

TABLE 4

| | EC$_{50}$ (nM) |
| --- | --- |
| S4 | 14.83 |
| S10 | 14.22 |
| S24 | 19.83 |
| S47 | 15.31 |
| S108 | 14.69 |
| S113 | 9.42 |
| S170 | 20.25 |
| S309 | 8.88 |
| #34 | ND |

<Example 4> To Evaluate Potential of Anti-PAD2 Antibody to Inhibit Citrullination The following conditions were used to measure the potential of each anti-PAD2 antibody to inhibit citrullination activity of calcium-bound PAD2.

(4-1) Materials

Recombinant protein: crude fraction containing the full-length recombinant human PAD2.

Substrate: BAEE (Na-benzoyl-L-arginine ethyl ester hydrochloride).

Antibodies: an anti-dinitrophenyl (DNP) antibody (a negative control), anti-PAD2 antibodies (S4, S10, S24, S47, S108, S113, S170, and S309), an anti-PAD2 antibody disclosed in WO/2014/086365 (#2).

(4-2) Protocol

First, 5 μL of 3.75 ng/μL (50 nM) human PAD2 was prepared and mixed with Tris-HCl buffer (pH 7.6), NaCl, and DTT in the total volume of 29 μL. To the resulting solution was added 5 μL of CaCl$_2$), and the mixture was allowed to stand at room temperature for 30 min. To the mixture were added, at the same time, 10 μL of antibody solution containing each anti-PAD2 antibody produced (S4, S10, S24, S47, S108, S113, S170, S309), #2 antibody, or anti-DNP antibody (negative control) at 0.5-3000 nM, 5 μL of 100 mM BAEE (benzoyl-arginine ethyl ester), and 1 μL of water. The resulting solution was then mixed well. This solution had a total volume of 50 μL and contained, as the final concentration, 20 mM Tris-HCl (pH 7.6), 150 mM NaCl, 1 mM DTT, 10 mM BAEE, 1 mM CaCl$_2$), 5 nM human PAD2, and each antibody at 0.1-600 nM. The solution was allowed to stand at 37° C. for 4 h. Then, 12.5 μL of 5 M perchloric acid was added to stop the reaction. The resulting citrullinated BAEE contained in this solution was subjected to colorimetry.

(4-3) Results

Table 5 shows the antibody concentration (EC$_{25}$) that imparted 25% activity inhibition to human PAD2. The case where the antibody concentration was below 600 nM and it was impossible to calculate the antibody concentration that imparted 25% activity inhibition was denoted as ND (Not Determined). With respect to the citrullination activity of calcium-bound PAD2, it was demonstrated that the antibodies such as S4, etc., had a higher potential to inhibit the activity than #2 antibody.

TABLE 5

| | EC$_{25}$ (nM) |
| --- | --- |
| S4 | 16.7 |
| S10 | 3.5 |
| S24 | 86.9 |
| S47 | 5.4 |
| S108 | 4.9 |
| S113 | 2.9 |
| S170 | 160.9 |

<table>
<tr><th>19</th><th>20</th></tr>
</table>

TABLE 5-continued

| | EC$_{25}$ (nM) |
|---|---|
| S309 | 7.2 |
| #2 | ND |

<Example 5> To Evaluate Potential of Anti-PAD2
Antibody to Inhibit Citrullination The following conditions were used to measure the potential of each anti-PAD2 antibody to inhibit citrullination activity of PAD2. At this time, a calf-thymus-derived histone was used as a substrate.

(5-1) Materials

Recombinant protein: crude fraction containing the full-length recombinant human PAD2.

Substrate: calf-thymus-derived histone

Antibodies: an anti-dinitrophenyl (DNP) antibody (a negative control), anti-PAD2 antibodies (S4, S10, S24, S47, S108, S113, and S170), anti-PAD2 antibodies disclosed in WO/2014/086365 (#2 and #34).

(5-2) Protocol

First, 5 µL of antibody solution was prepared using each anti-PAD2 antibody (S4, S10, S24, S47, S108, S113, S170), #2 or #34 antibody, or anti-DNP antibody (negative control) at 1 to 6000 nM. Next, 5 µL of 3.75 ng/µL (50 nM) human PAD2 was prepared. Then, these solution, Tris-HCl buffer (pH 7.6), NaCl, and DTT were mixed in the total volume of 44 µL. The resulting solution was allowed to stand for 30 min. After that, 5 µL of calf-thymus-derived histone and 1 µL of 0.05 M CaCl$_2$) were added and mixed well at the same time. This solution had a total volume of 50 µL and contained, as the final concentration, 20 mM Tris-HCl (pH 7.6), 150 mM NaCl, 1 mM DTT, 1.8 mg/mL histone, 1 mM CaCl$_2$), 5 nM human PAD2, and each antibody at 0.1-600 nM. The solution was allowed to stand at 37° C. for 4 h. Then, 12.5 µL of 5 M perchloric acid was added to stop the reaction. The resulting citrullinated calf-thymus-derived histone contained in this solution was subjected to colorimetry.

(5-3) Results

Table 6 shows the antibody concentration (EC$_{50}$) that imparted 50% activity inhibition to human PAD2. The case where the antibody concentration was below 600 nM and it was impossible to calculate the antibody concentration that imparted 50% activity inhibition was denoted as ND (Not Determined). The antibodies such as S4, etc., were demonstrated to have a higher potential to inhibit the activity than #2 and #34 antibodies.

TABLE 6

| | EC$_{50}$ (nM) |
|---|---|
| S4 | 14.7 |
| S10 | 7.6 |
| S24 | 15.2 |
| S47 | 7.5 |
| S108 | 8.2 |
| S113 | 6.2 |
| S170 | 16.5 |
| #2 | 150.8 |
| #34 | ND |

<Example 6> To Evaluate Citrullination
Activity-Inhibitory Function of Anti-PAD2
Antibody The following conditions were used to measure the potential of each anti-PAD2 antibody to inhibit citrullination activity of PAD2. At this time, bovine myelin basic protein was used as a substrate.

(6-1) Materials

Recombinant protein: crude fraction containing the full-length recombinant human PAD2.

Substrate; bovine myelin basic protein

Antibodies: an anti-dinitrophenyl (DNP) antibody (a negative control), anti-PAD2 antibodies (S4, S10, S24, S47, S108, S113, S170, and S309), anti-PAD2 antibodies disclosed in WO/2014/086365 (#2 and #34).

(6-2) Protocol

First, 5 µL of antibody solution was prepared using each anti-PAD2 antibody (S4, S10, S24, S47, S108, S113, S170, S309), #2 or #34 antibody, or anti-DNP antibody (negative control) at 6000 nM. Next, 5 µL of 3.75 ng/µL (50 nM) human PAD2 was prepared. Then, these solution, Tris-HCl buffer (pH 7.6), NaCl, and DTT were mixed in the total volume of 44 µL. The resulting solution was allowed to stand for 30 min. After that, 5 µL of bovine myelin basic protein and 1 µL of 0.05 M CaCl$_2$) were added and mixed well at the same time. This solution had a total volume of 50 µL and contained, as the final concentration, 20 mM Tris-HCl (pH 7.6), 150 mM NaCl, 1 mM DTT, 1.8 mg/mL bovine myelin basic protein, 1 mM CaCl$_2$), 5 nM human PAD2, and each antibody at 600 nM. The solution was allowed to stand at 37° C. for 4 h. Then, 12.5 µL of 5 M perchloric acid was added to stop the reaction. The resulting citrullinated bovine myelin basic protein contained in this solution was subjected to colorimetry.

(6-3) Results

Figure 2:
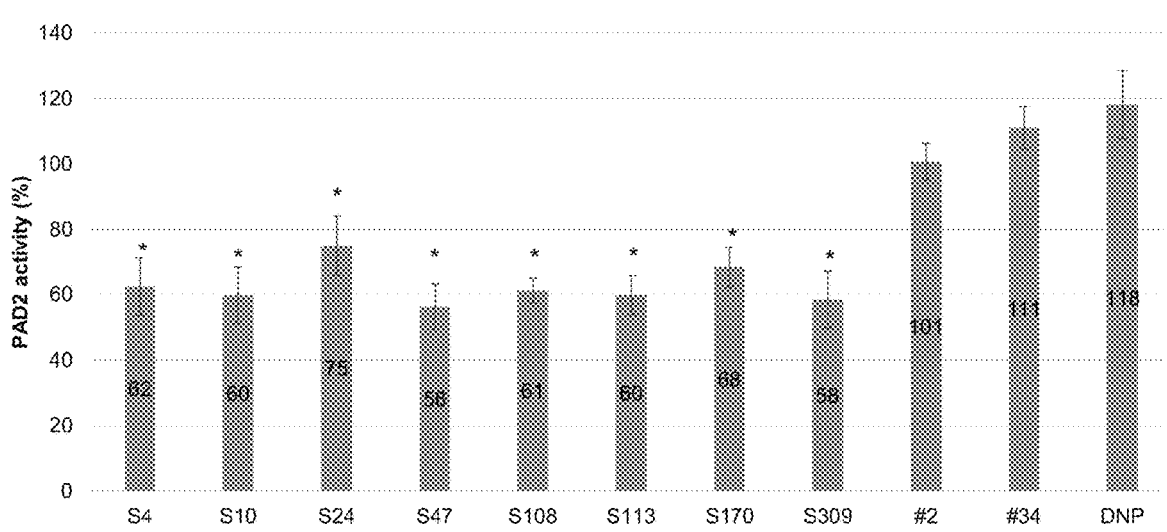
FIG. 2 is a graph showing the results of measuring citrullination activity of human PAD2 when each anti-PAD2 antibody used in Examples was added. The case where the antibody caused a significant difference by a (two-tailed) t-test when compared with an anti-DNP antibody (negative control) is marked by * ($p < 0.01$).

FIG. 2 shows the results of measuring the citrullination activity of human PAD2 when each antibody was added. The values in FIG. 2 are the average and the standard deviation while the value for TBS was set to 100%. The #2 and #34 antibodies had no inhibitory activity detected. By contrast, the antibodies such as S4, etc., exhibited high inhibitory activity. The antibody exhibiting a significant difference from the anti-DNP antibody (negative control) was marked with *(p<0.01).

<Example 7> To Assess Epitope (7-1) Procedure

Three consecutive amino acids of the amino acid residues of an antigen sequence (YLNRGDRWIQDEIEFGY; SEQ ID NO: 1) were replaced by alanine residues to synthesize six Ala mutants (SEQ ID NOs: 3 to 8). How each Ala mutant reacted with each anti-PAD2 antibody produced (S4, S10, S24, S108, S170, S309) was assessed (by ELISA) to determine, as an epitope, amino acid residues before Ala replacement in an Ala mutant toward which each antibody such as S4, etc., did not exhibit significant reactivity.

```
(7-2) Ala mutants
                              (SEQ ID NO: 3)
AAARGDRWIQDEIEFGY (SEQ ID NO: 4)
YLNAAARWIQDEIEFGY (SEQ ID NO: 5)
YLNRGDAAAQDEIEFGY (SEQ ID NO: 6)
YLNRGDRWIAAAIEFGY (SEQ ID NO: 7)
YLNRGDRWIQDEAAAGY (SEQ ID NO: 8)
YLNRGDRWIQDEIEFAA
```

(7-3) Experimental Conditions

TABLE 7

| 1 Antigen immobilized: | 50 μL/well | O/N, @ 4° C. | 10 μg/mL Peptide |
|---|---|---|---|
| 2 Blocking: | 250 μL/well | 60 min, @ 37° C. | 25% Block Ace/PBS |
| 3 Primary antibody: | 50 μL/well | 90 min, @ 37° C. | 200 ng/mL of each antibody diluted 4-fold with 10% Block Ace/PBS |
| 4 Secondary antibody: | 50 μL/well | 90 min, @ 37° C. | HRP-anti-mouse IgG (H + L) in 10% Block Ace/PBS (1:1000) |
| 5 Chromogenic substrate: | 50 μL/well | 30 min, @ RT | TMB (manufactured by KPL, Inc.) |
| 6 To stop coloring: | 50 μL/well | | TMB-stop solution (manufactured by KPL, Inc.) |
| 7 Measurement: | Wavelength at 450 nm/650 nm | | |
| 8 To calculate $EC_{50}$ | Analysis software SoftMax Pro 6.5 (manufactured by Molecular Devices, Inc.) was used for calculation | | |

(7-4) Results

FIG. 3 shows the values for 50% effective concentration ($EC_{50}$) of S4, etc., with respect to each Ala mutant or the original antigen sequence. The results have revealed that S4, etc., did not exhibit significant reactivity toward Ala mutants with mutations at positions corresponding to some of positions 344 to 357 of PAD2. This has demonstrated that S4, etc., recognizes, in particular, amino acids within positions 344 to 357 among positions 341 to 357 of PAD2.

The above Examples have made it clear that the antibodies that can bind to positions 341 to 357 of PAD2 exerted excellent activity of inhibiting citrullination by PAD2.

Hereinabove, the invention has been described based on the Examples. The Examples are just examples. Those skilled in the art should understand that various modifications are allowed and such modified embodiments are within the scope of the invention.

The invention claimed is:

1. A peptide, wherein the amino acid sequence of the peptide consists of the amino acid sequence set forth in SEQ ID NO: 1.

2. The peptide according to claim 1, wherein the peptide is further chemically modified.

3. A composition comprising the peptide according to claim 1 in isolated, purified, or concentrated form.

4. An antigen composition comprising the peptide according to claim 1.

5. The composition according to claim 4, comprising a buffer or adjuvant.

6. A method for producing an anti-PAD2 antibody, comprising the step of immunizing a mammal or bird with the peptide according to claim 1.

7. An anti-PAD2 antibody that specifically binds to the peptide according to claim 1.

8. An anti-PAD2 antibody that specifically binds to the peptide according to claim 2.

9. The anti-PAD2 antibody according to claim 7, wherein the antibody inhibits PAD2 activity.

10. The anti-PAD2 antibody according to claim 9, wherein KD (M) toward the PAD2 is $9.0 \times 10^{-8}$ or less.

11. The anti-PAD2 antibody according to claim 9, wherein the antibody specifically binds to positions 344 to 357 of PAD2.

12. The anti-PAD2 antibody according to claim 9, which is a monoclonal antibody.

13. The anti-PAD2 antibody according to claim 10, which is a monoclonal antibody.

14. The anti-PAD2 antibody according to claim 7, which is an antigen-binding fragment.

15. The anti-PAD2 antibody according to claim 8, wherein the antibody inhibits PAD2 activity.

16. The anti-PAD2 antibody according to claim 15, wherein KD (M) toward the PAD2 is $9.0 \times 10^{-8}$ or less.

17. The anti-PAD2 antibody according to claim 15, wherein the antibody specifically binds to positions 344 to 357 of PAD2.

18. The anti-PAD2 antibody according to claim 15, which is a monoclonal antibody.

19. The anti-PAD2 antibody according to claim 16, which is a monoclonal antibody.

20. The anti-PAD2 antibody according to claim 8, which is an antigen-binding fragment.

21. A method for inhibiting PAD2 activity, comprising the step of causing PAD2 to contact the anti-PAD2 antibody according to claim 7.

22. A method for inhibiting PAD2 activity, comprising the step of causing PAD2 to contact the anti-PAD2 antibody according to claim 8.

23. A method for promoting a function of a composition to inhibit PAD2 activity, comprising the step of increasing, in the composition, a ratio of the anti-PAD2 antibody according to claim 7.

24. A method for promoting a function of a composition to inhibit PAD2 activity, comprising the step of increasing, in the composition, a ratio of the anti-PAD2 antibody according to claim 8.

25. The anti-PAD2 antibody of claim 7, which is a monoclonal antibody.

* * * * *

SEQUENCE LISTING

```
<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: Peptide

<400> SEQUENCE: 1

Tyr Leu Asn Arg Gly Asp Arg Trp Ile Gln Asp Glu Ile Glu Phe Gly
1               5                   10                  15

Tyr

<210> SEQ ID NO 2
<211> LENGTH: 665
<212> TYPE: PRT
<213> ORGANISM: Homo sapiens

<400> SEQUENCE: 2

Met Leu Arg Glu Arg Thr Val Arg Leu Gln Tyr Gly Ser Arg Val Glu
1               5                   10                  15

Ala Val Tyr Val Leu Gly Thr Tyr Leu Trp Thr Asp Val Tyr Ser Ala
                20                  25                  30

Ala Pro Ala Gly Ala Gln Thr Phe Ser Leu Lys His Ser Glu His Val
            35                  40                  45

Trp Val Glu Val Val Arg Asp Gly Glu Ala Glu Glu Val Ala Thr Asn
        50                  55                  60

Gly Lys Gln Arg Trp Leu Leu Ser Pro Ser Thr Thr Leu Arg Val Thr
65                  70                  75                  80

Met Ser Gln Ala Ser Thr Glu Ala Ser Ser Asp Lys Val Thr Val Asn
                85                  90                  95

Tyr Tyr Asp Glu Glu Gly Ser Ile Pro Ile Asp Gln Ala Gly Leu Phe
                100                 105                 110
```

-continued

```
Leu Thr Ala Ile Glu Ile Ser Leu Asp Val Asp Ala Asp Arg Asp Gly
        115                 120                 125

Val Val Glu Lys Asn Asn Pro Lys Lys Ala Ser Trp Thr Trp Gly Pro
        130                 135                 140

Glu Gly Gln Gly Ala Ile Leu Leu Val Asn Cys Asp Arg Glu Thr Pro
145                 150                 155                 160

Trp Leu Pro Lys Glu Asp Cys Arg Asp Glu Lys Val Tyr Ser Lys Glu
                165                 170                 175

Asp Leu Lys Asp Met Ser Gln Met Ile Leu Arg Thr Lys Gly Pro Asp
            180                 185                 190

Arg Leu Pro Ala Gly Tyr Glu Ile Val Leu Tyr Ile Ser Met Ser Asp
            195                 200                 205

Ser Asp Lys Val Gly Val Phe Tyr Val Glu Asn Pro Phe Phe Gly Gln
        210                 215                 220

Arg Tyr Ile His Ile Leu Gly Arg Arg Lys Leu Tyr His Val Val Lys
225                 230                 235                 240

Tyr Thr Gly Gly Ser Ala Glu Leu Leu Phe Phe Val Glu Gly Leu Cys
                245                 250                 255

Phe Pro Asp Glu Gly Phe Ser Gly Leu Val Ser Ile His Val Ser Leu
            260                 265                 270

Leu Glu Tyr Met Ala Gln Asp Ile Pro Leu Thr Pro Ile Phe Thr Asp
        275                 280                 285

Thr Val Ile Phe Arg Ile Ala Pro Trp Ile Met Thr Pro Asn Ile Leu
        290                 295                 300

Pro Pro Val Ser Val Phe Val Cys Cys Met Lys Asp Asn Tyr Leu Phe
305                 310                 315                 320

Leu Lys Glu Val Lys Asn Leu Val Glu Lys Thr Asn Cys Glu Leu Lys
                325                 330                 335

Val Cys Phe Gln Tyr Leu Asn Arg Gly Asp Arg Trp Ile Gln Asp Glu
            340                 345                 350

Ile Glu Phe Gly Tyr Ile Glu Ala Pro His Lys Gly Phe Pro Val Val
        355                 360                 365

Leu Asp Ser Pro Arg Asp Gly Asn Leu Lys Asp Phe Pro Val Lys Glu
        370                 375                 380

Leu Leu Gly Pro Asp Phe Gly Tyr Val Thr Arg Glu Pro Leu Phe Glu
385                 390                 395                 400

Ser Val Thr Ser Leu Asp Ser Phe Gly Asn Leu Glu Val Ser Pro Pro
                405                 410                 415

Val Thr Val Asn Gly Lys Thr Tyr Pro Leu Gly Arg Ile Leu Ile Gly
            420                 425                 430

Ser Ser Phe Pro Leu Ser Gly Gly Arg Arg Met Thr Lys Val Val Arg
        435                 440                 445

Asp Phe Leu Lys Ala Gln Gln Val Gln Ala Pro Val Glu Leu Tyr Ser
        450                 455                 460

Asp Trp Leu Thr Val Gly His Val Asp Glu Phe Met Ser Phe Val Pro
465                 470                 475                 480

Ile Pro Gly Thr Lys Lys Phe Leu Leu Leu Met Ala Ser Thr Ser Ala
                485                 490                 495

Cys Tyr Lys Leu Phe Arg Glu Lys Gln Lys Asp Gly His Gly Glu Ala
            500                 505                 510

Ile Met Phe Lys Gly Leu Gly Gly Met Ser Ser Lys Arg Ile Thr Ile
            515                 520                 525

Asn Lys Ile Leu Ser Asn Glu Ser Leu Val Gln Glu Asn Leu Tyr Phe
```

-continued

```
         530                535                540
Gln Arg Cys Leu Asp Trp Asn Arg Asp Ile Leu Lys Lys Glu Leu Gly
545                550                555                560

Leu Thr Glu Gln Asp Ile Ile Asp Leu Pro Ala Leu Phe Lys Met Asp
                565                570                575

Glu Asp His Arg Ala Arg Ala Phe Phe Pro Asn Met Val Asn Met Ile
                580                585                590

Val Leu Asp Lys Asp Leu Gly Ile Pro Lys Pro Phe Gly Pro Gln Val
            595                600                605

Glu Glu Glu Cys Cys Leu Glu Met His Val Arg Gly Leu Leu Glu Pro
        610                615                620

Leu Gly Leu Glu Cys Thr Phe Ile Asp Asp Ile Ser Ala Tyr His Lys
625                630                635                640

Phe Leu Gly Glu Val His Cys Gly Thr Asn Val Arg Arg Lys Pro Phe
                645                650                655

Thr Phe Lys Trp Trp His Met Val Pro
            660                665

<210> SEQ ID NO 3
<211> LENGTH: 17
<212> TYPE: PRT
<213> ORGANISM: Artificial Sequence
<220> FEATURE:
<223> OTHER INFORMATION: Peptide

<400> SEQUENCE: 3

Ala Ala Ala Arg Gly Asp Arg Trp Ile Gln Asp Glu Ile Glu Phe Gly
1                5                10                15

Tyr

<210> SEQ ID NO 4
<211> LENGTH: 17
<212> TYPE: PRT
<213> ORGANISM: Artificial Sequence
<220> FEATURE:
<223> OTHER INFORMATION: Peptide

<400> SEQUENCE: 4

Tyr Leu Asn Ala Ala Ala Arg Trp Ile Gln Asp Glu Ile Glu Phe Gly
1                5                10                15

Tyr

<210> SEQ ID NO 5
<211> LENGTH: 17
<212> TYPE: PRT
<213> ORGANISM: Artificial Sequence
<220> FEATURE:
<223> OTHER INFORMATION: Peptide

<400> SEQUENCE: 5

Tyr Leu Asn Arg Gly Asp Ala Ala Ala Gln Asp Glu Ile Glu Phe Gly
1                5                10                15

Tyr

<210> SEQ ID NO 6
<211> LENGTH: 17
<212> TYPE: PRT
<213> ORGANISM: Artificial Sequence
<220> FEATURE:
<223> OTHER INFORMATION: Peptide
```

-continued

```
<400> SEQUENCE: 6

Tyr Leu Asn Arg Gly Asp Arg Trp Ile Ala Ala Ala Ile Glu Phe Gly
1               5                   10                  15

Tyr

<210> SEQ ID NO 7
<211> LENGTH: 17
<212> TYPE: PRT
<213> ORGANISM: Artificial Sequence
<220> FEATURE:
<223> OTHER INFORMATION: Peptide

<400> SEQUENCE: 7

Tyr Leu Asn Arg Gly Asp Arg Trp Ile Gln Asp Glu Ala Ala Ala Gly
1               5                   10                  15

Tyr

<210> SEQ ID NO 8
<211> LENGTH: 17
<212> TYPE: PRT
<213> ORGANISM: Artificial Sequence
<220> FEATURE:
<223> OTHER INFORMATION: Peptide

<400> SEQUENCE: 8

Tyr Leu Asn Arg Gly Asp Arg Trp Ile Gln Asp Glu Ile Glu Phe Ala
1               5                   10                  15

Ala
```